United States Patent [19]

Borchardt et al.

[11] Patent Number: 4,859,677

[45] Date of Patent: Aug. 22, 1989

[54] NUCLEOSIDE ANALOGUES HAVING ANTIVIRAL ACTIVITY

[75] Inventors: Ronald T. Borchardt; David R. Borcherding, both of Lawrence, Kans.

[73] Assignee: University of Kansas, Lawrence, Kans.

[21] Appl. No.: 39,511

[22] Filed: Apr. 17, 1987

[51] Int. Cl.$^4$ .................. A61K 31/52; A61K 31/435; C07D 473/34; C07D 471/02

[52] U.S. Cl. .................................. 514/261; 514/303; 544/277; 546/118

[58] Field of Search ................ 544/277; 514/261, 303; 546/118

[56] References Cited

U.S. PATENT DOCUMENTS

| | | | |
|---|---|---|---|
| 3,825,541 | 7/1974 | Vince | 544/277 |
| 3,917,837 | 11/1975 | Lin et al. | 514/261 |
| 4,199,574 | 4/1980 | Schaeffer | 544/277 X |
| 4,321,376 | 3/1982 | Otani et al. | 544/277 |
| 4,423,218 | 12/1983 | Otani et al. | 544/277 |
| 4,613,666 | 9/1986 | Fukukawa et al. | 544/277 |

FOREIGN PATENT DOCUMENTS 0219284  12/1984  Japan .................. 514/261

OTHER PUBLICATIONS

Arita, et al., "J. Am. Chem. Soc.", vol. 105, No. 12, pp. 4049–4055 (1983).
Keller, et al., "Biological Methylation and Drug Design", The Humana Press, 1986, pp. 385–396.
Matuszewska, et al., Journal of Biological Chemistry, vol. 262(1), pp. 265–268, 01/05/87.
Hasobe, et al., Antimicrobial Agents and Chemotherapy, vol. 31(1), pp. 1849–1851, Nov. 1987.
Hasobe, et al., Molecular Pharmacology, vol. 33, pp. 713–720 (1988).
Fisher, et al., Journal of Antibiotics, vol. 40(6), pp. 873–881 (06/87).
Trost, et al., Chemical Abstracts, vol. 108, No. 7, 56522n (1988).
Borcherding, et al., Chemical Abstracts, vol. 107(25):237204k, (1987), Abstract of J. Org. Chem., vol. 52(54), pp. 5457–5461 (1987).
Hasobe, et al., Chemical Abstracts, vol. 108(5):31319p (1987), Abstract of Antimicrob. Agents Chemother., vol. 31(11), pp. 1849–1851 (1987).
Narayanan, et al., Chemical Abstracts, vol. 108(11):90734t (1988), Abstract of J. Med. Chem., vol. 31(3), pp. 500–503 (1988).
Akimoto et al., J. Med. Chem., 29, 1749–1753 (1986).
Beer et al., Helvetica Chimica Acta, vol. 65, 2570–2582 (1982).
Chamberlin et al., J. Org. Chem., 50, 4425–4431 (1985).
De Clercq, Antimicrobial Agents and Chemotherapy, vol. 28, No. 1, 84–89 (Jul. 1985).
Guthrie et al., J. Chem. Soc., 853–854 (1959).
Haines et al., J. Med. Chem., 30, 943–947 (1987).
Hua et al., J. Med. Chem., 30, 198–200 (1987).
Hudlicky et al., American Chemical Society Div. of Organic Chem., 193rd ACS Natl. Meeting, Denver, CO, Apr. 5–10, 1987.
Iwakawa et al., Can. J. of Chem., 56, 326–335 (1978).
Johnson et al., J. Am. Chem. Soc., 108, 5655–5656 (1986).
Krenitsky et al., J. Med. Chem., 29, 138–143 (1986).
Phadtare et al., J. Med. Chem., 30, 437–440 (1987).

Primary Examiner—Anton H. Sutto
Assistant Examiner—Diana G. Rivers
Attorney, Agent, or Firm—Birch, Stewart, Kolasch & Birch

[57] ABSTRACT

Compounds of the formula (I)

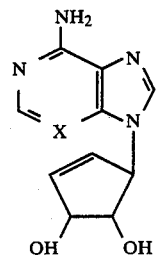

wherein X is =N— or =CH— and physiologically acceptable salts and solvents thereof which have antiviral activity, a process for the preparation of the compounds and intermediates thereof, pharmaceutical compositions containing the compounds and a method for inhibiting the propagation of virus using the compounds.

16 Claims, No Drawings

NUCLEOSIDE ANALOGUES HAVING ANTIVIRAL ACTIVITY

TECHNICAL FIELD

The present invention relates to antiviral compounds which inhibit viral replication, a process for their preparation, a process for preparing intermediates thereof, pharmaceutical compositions containing them and their use in medicine.

PRIOR ART

Existing treatments for viral infections include the administration of chemical compounds which are nucleoside analogues, for example, 2'-deoxy-5-iodouridine, 9-(2-hydroxyethoxymethyl)guanine and 9-beta-D-arabinofuranosyladenine. There is, however, a need for compounds with improved antiviral activity and this has stimulated further research in attempts to find nucleoside analogues which have improved properties. A group of naturally occurring adenine derivatives known as "neplanocins" have been shown to have antiviral activity, E. DeClercq, *Antimicrob. Agents Chemother.*, 28, 84–89 (July 1985). Neplanocin A ((−)-9-[trans-2',trans-3'-dihydroxy-4'-(hydroxymethyl)-cyclopent-4'-enyl]-adenine) is a cyclopentenyl analog of adenosine which has been shown to have broad spectrum antiviral activity. However, its antiviral effectiveness is limited by its cytotoxicity.

A process for producing (+)2,3-5-cyclohexylidenedioxy-4-cyclopentenone, which is useful as an intermediate in prostaglandin synthesis or the queuine base of nucleoside Q, is disclosed by Johnson et al, *J. Chem. Soc.*, 108, 5655–5656 (1986) and Akimoto et al, *J. Med. Chem.*, 29, 1749–1753 (1986).

SUMMARY OF THE INVENTION

The present invention is directed to compounds of the formula (I)

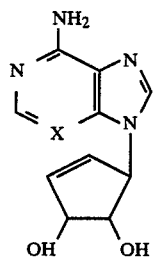

(I)

wherein X is =N— or =CH— and physiologically acceptable salts and solvates thereof which have antiviral activity, a process for preparing the compounds and intermediates thereof, pharmaceutical compositions containing the compounds and a method for inhibiting the propagation of virus using the compounds.

Physiologically acceptable salts include acid addition salts formed with organic or inorganic acids, for example, hydrochlorides, hydrobromides, sulphates such as creatine sulphate salts, phosphates, citrates, fumarates and maleates. The invention includes within its scope biological precursors of the compounds of formula (I) and their physiologically acceptable salts with acids, e.g., metabolically labile esters which are converted in vivo to the parent compound. It is to be understood that the present invention encompasses the individual (+) and (−) stereochemical configuration of the compounds of formula (I) as well as wholly or partially racemic mixtures of such isomers.

The preferred compounds have the following (−) stereochemical configuration

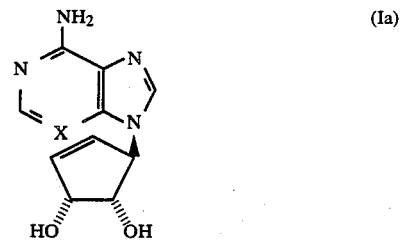

(Ia)

wherein X is as defined above.

Specifically, the invention relates to (−)6-amino-9-[trans-2',trans-3'-dihydroxycyclopent-4,-enyl]-purine and (−)4-amino-1-[trans-2',trans-3'-dihydroxycyclopent-4'-enyl]-imidazo[4,5c]pyridine and physiologically acceptable salts and solvates thereof.

The activity of the compounds of the formula (Ia) against vaccinia virus in vitro (in L929 cells) has been established. It can be expected that the compounds of the formula (I) may be active in vitro and in vivo against DNA viruses such as poxviruses (i.e. vaccinia), double strand (+) RNA viruses (i.e. reo) and single strand (−) RNA viruses (i.e. measles, parainfluenza and vesicular stomatitis). The compounds of the invention have been shown to have a low level of cytotoxicity.

The compounds of the present invention could be used for the treatment and/or prophylaxis of human and animal diseases, particularly mammalian diseases, caused by the above-mentioned viruses and possibly other viruses. It is contemplated that the invention compounds will be formulated into a pharmaceutical composition comprising an effective antiviral amount of the compound of the formula (I) and a pharmaceutically acceptable carrier. An effective antiviral amount of the pharmaceutical composition will be administered to the subject, human, animal or mammal, in a manner which inhibits or prevents viral replication. The amount of the compound (I) and the specific pharmaceutically acceptable carrier will vary depending upon the mode of administration and the type of viral condition being treated.

In a particular aspect the pharmaceutical composition comprises a compound of formula (I) in effective unit dosage form. As used herein the term "effective unit dosage" or "effective unit dose" is denoted to mean a predetermined antiviral amount sufficient to be effective against the viral organisms in vivo. Pharmaceutically acceptable carriers are materials useful for the purpose of administering the medicament, which are preferably non-toxic, and may be solid, liquid or gaseous materials, which are otherwise inert and medically acceptable and are compatible with the active ingredients. The pharmaceutical compositions may contain other active ingredients such as antimicrobial agents and other agents such as preservatives.

These pharmaceutical compositions may be administered parenterally, including by injection, orally, used as a suppository or pessary, applied topically as an ointment, cream, aerosol, powder, or given as eye or nose drops etc., depending on whether the preparation is used to treat internal or external viral infections.

The compositions may contain 0.1%–99% of the active material. For topical administration, for example, the composition will generally contain from 0.01% to 20%, more preferably 0.5% to 5% of the active material.

For oral administration, fine powders or granules may contain diluting, dispersing and/or surface active agents, and may be presented in a draught, in water or in a syrup; in capsules or sacnets in the dry state or in a non-aqueous solution or suspension, wherein suspending agents may be included; in tablets, wherein binders and lubricants may be included; or in a suspension in water or a syrup. Where desirable or necessary, flavouring, preserving, suspending, thickening or emulsifying agents may be included. Tablets and granules are preferred, and these may be coated.

For buccal administration the compositions may take the form of tablets or lozenges formulated in a conventional manner.

For parenteral administration or for administration as drops, as for eye infections, the compounds may be presented in aqueous solution in a concentration of from about 0.1 to 10% more preferably 0.5 to 2.0%, most preferably 1.2% w/v. The solution may contain antioxidants, buffers, etc.

The compounds according to the invention may also be formulated for injection and may be presented in unit dose form in ampoules or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for consitution with a suitable vehicle, e.g., sterile, pyrogen-free water, before use.

Alternatively for infections of the eye, or other external tissues, e.g., mouth and skin, the compositions are preferably applied to the infected part of the body of the patient as a topical ointment or cream. The compounds may be presented in an ointment, for instance with a water soluble ointment base, or in a cream, for instance with an oil in water cream base, in a concentration of from about 0.1 to 10%; preferably 0.5 to 2.0%, most preferably 1.2% w/v.

The compounds may also be applied into body orifices such as the nose, oral cavity and ears in the form of a spray or drops. They may be applied into body orifices such as the rectum and vagina in the form of a suppository or cream.

For topical administration the daily dosage as employed for adult human treatment will range from 0.1 mg to 1000 mg, preferably 0.5 mg and 10 mg. However, it will be appreciated that extensive skin infections may require the use of higher doses.

For systemic administration the daily dosage as employed for adult human treatment will range from 5 mg to 5000 mg, preferably 50 mg to 2000 mg, which may be administered in 1 to 5 daily doses, for example, depending on the route of administration and the condition of the patient. When the compositions comprise dosage units, each unit will preferably contain 2 mg to 2000 mg of active ingredient, for example 50 mg to 500 mg. For serious infections the compound may be administered by intravenous infusion using, for example, 0.01 to 10 mg/kg/hr of the active ingredient.

In yet a further aspect of the invention there is provided a method of treating or preventing viral infections in mammals which comprises the administration of an effective antiviral amount, as hereinbefore defined, of a compound of formula (I), or physiologically acceptable salt thereof.

The compounds of the present invention of the formula (I) can be produced by a process which comprises:
reacting a compound of the formula (II)

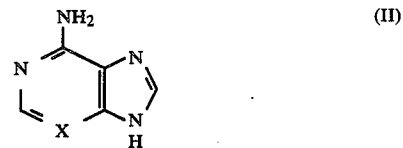

or a salt or reactive derivative thereof wherein X is =N— or =CH— with a compound of the formula (III)

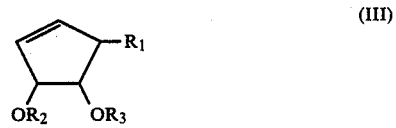

wherein $R_1$ is a leaving group and $R_2$ and $R_3$ are each a hydroxy protecting group or $R_2$ and $R_3$ together form a hydroxy protecting group to form a compound of the formula (IV)

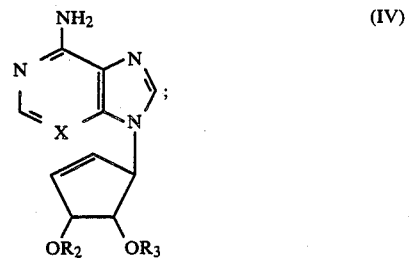

optionally deprotecting compound (IV) to form a compound of the formula (I); and
optionally forming a physiologically acceptable salt of the compound of the formula (I).

Salts of the compounds of the formula (II) which may be used in the reaction include metallic salts, preferably alkali metal salts such as sodium, potassium and lithium salts.

The leaving group $R_1$ may be any group which can be removed when compound (II) is reacted with compound (III). For example, $R_1$ can be a sulfonoxy group such as para-toluenesulfonyloxy or methanesulfonoxy, a halide such as chlorine, bromine or iodine or a hydroxyl group. If $R_1$ is a sulfonoxy or halogen group, then the salt of compound (II) should preferably be used in the reaction. If $R_1$ is a hydroxyl group, then the compound (II) (not the salt thereof) should preferably be reacted with compound (III) in the presence of triphenylphosphine and diethyl azodicarboxylate (DEAD) in accordance with the procedure reported by Iwakawa et al, Can. J. Chem., 56, 326–335 (1978).

Where any of $R_2$ and $R_3$ represents a protecting group, the protecting group may be any conventional protecting group, for example as described in "Protective Groups in Organic Chemistry" Ed. J. F. W. McOmie (Plenum Press 1973) or "Protective Groups in Organic Synthesis" by Theodora W. Greene (John Wiley and Sons 1981). Examples of suitable protecting groups include alkyl groups such as methyl, t-butyl and methoxymethyl groups; aralkyl groups such as benzyl, diphenylmethyl, triphenylmethyl and p-methoxyphenyldiphenylmethyl groups; acyl groups, e.g., hydrocarbylcarbonyl groups such as benzoyl, pivaloyl, octanoyl and acetyl groups; and silyl groups such as trialkylsilyl group, e.g., a t-butyldimethylsilyl group. In addition, $R_2$ and $R_3$ may together represent a protecting group. Thus, for example, $R_2$ and $R_3$ may together represent an alkylidene or cycloalkylidene group, e.g., an isopropylidene group or a cyclohexylidene group, or $R_2$ and $R_3$ may together represent a disiloxanyl group for example 1,1,3,3-tetraisopropyldisilox-1,3-diyl.

The reaction of compound (II) and compound (III) is carried out under any conditions which allow formation of a recoverable quantity of compound (IV). The reaction is preferably a liquid phase reaction carried out in a polar aprotic solvent such as dimethylformamide, dimethylsulfoxide or acetonitrile at a temperature of 0° to 150° C.; preferably 20° to 90° C. for 1 hour to 7 days, preferably 1 to 2 days. The molar ratio of compound (II) to compound (III) is usually 0.5–10:1, preferably an excess of compound (II) such as 1.1–5:1 so that all of compound (III) is used up during the reaction.

Deprotection can be achieved using conventional techniques such as those described in "Protective Groups in Organic Chemistry" Ed. J. F. W. McOmie, supra and "Protective Groups in Organic Synthesis", supra. Thus, for example, an alkyl, acyl or silyl group may be removed by solvolysis, e.g., hydrolysis under acidic or basic conditions. For example, where $R_2$ and $R_3$ together represent an isopropylidene or cyclohexylidene group, this group may be removed by treatment with aqueous hydrogen chloride. A benzoyl group may be removed by treatment with methanolic ammonia. An aralkyl group may be cleaved by boron trichloride. Silyl groups, e.g., as mentioned above, may also conveniently be removed using a source of fluoride ions such as, e.g., tetra-n-butylammonium fluoride.

The deprotection step is usually carried out in the liquid phase in a polar protic solvent such as water or a water/alcohol mixture, e.g., a water/ethanol mixture at 0° to 100° C., preferably 20° to 100° C. for 1 to 10 hours, preferably 3 to 6 hours at an acidic pH, preferably a pH of 0 to 2.

However, it will be understood that, e.g., metabolically labile esters may have been chosen as protected groups $OR_2$ and/or $OR_3$ during the preparation of compounds of formula (I) in which case deprotection need not be effected to obtain compounds according to the invention.

The compounds of general formula (I) may, if desired, be converted into their physiologically acceptable salts and biological precursors according to conventional methods. Thus, the salts may be formed by reaction with an appropriate acid, if desired, in the presence of a solvent, e.g., with hydrogen chloride in ethanol. Metabolically labile esters may be formed by esterification using conventional techniques.

The present invention is also directed to a process comprising the following steps, either individually or collectively:

protecting the ring hydroxyl groups of ribonolactone (V)

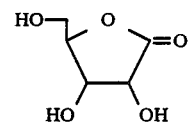

to form a compound of the formula (VI)

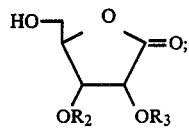

wherein $R_2$ and $R_3$ are as defined above;

converting compound (VI) into a compound of the formula (VII)

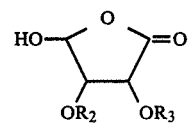

by the procedure reported in Beer et al, *Helvetica Chimica Acta*, 65, 2570 (1982);

reacting compound (VII) with an alcohol of the formula $R_4OH$ which prevents formation of an open chain ester of compound (VII) to form a compound of the formula (VIII)

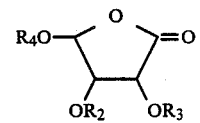

wherein $R_4$ is an alkyl group having at least two carbon atoms or an aryl group, preferably a $C_2$–$C_6$ alkyl group or a phenyl group, most preferably an isopropyl group, preferably in the presence of an acid catalyst having a pKa of 4.6 to 5.5 such as pyridinium aryl or alkyl sulfonate;

reacting (VIII) with a salt of dimethyl methylphosphonate, preferably an alkali metal salt such as a lithium salt, to form a compound of the formula (IX)

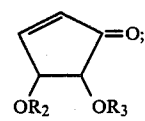

reducing (IX) by contacting (IX) with a reducing agent such as a sodium borohydride/cerium chloride complex ($NaHB_4/CeCl_3$), zinc borohydride ($ZnBH_4$) or diisobutylaluminum hydride (DIBAH) to form a compound of the formula (X)

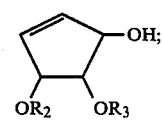

replacing the hydrogen of the hydroxyl group of (X) with a leaving group as defined above to produce a compound of the formula (III)

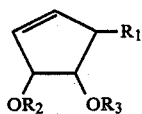  (III)

wherein R₁ is the leaving group;
reacting (III) with a compound of the formula (II)

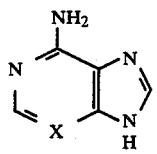  (II)

or a salt or reactive derivative thereof wherein X is as defined above to form a compound of the formula (IV)

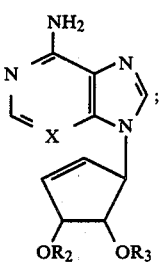  (IV)

and
deprotecting (IV) to form said compound of the formula (I)

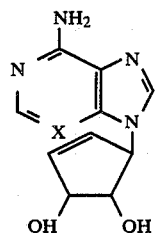  (I)

The present invention is also directed to a process for preparing enantiomerically pure compound (IXa)

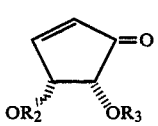  (IXa)

or its opposite enantiomer (IXb)

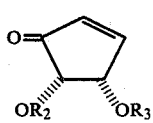  (IXb)

wherein R₂ and R₃ are as defined above which comprises:
reacting compound (VIIa) or (VIIb)

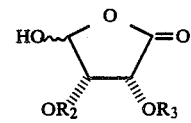  (VIIa)

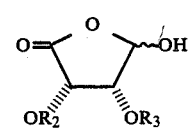  (VIIb)

with an alcohol of the formula R₄OH wherein R₄ is as defined above to produce enantiomerically pure compound (VIIIa) or (VIIIb), respectively

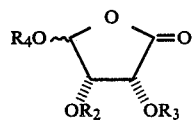  (VIIIa)

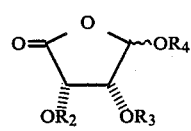  (VIIIb)

wherein R₄ is as defined above; and
reacting compound (VIIIa) or (VIIIb) with a salt of dimethyl methylphosphonate to produce enantiomerically pure compound (IXa) or (IXb), respectively.

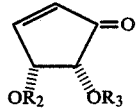  (IXa)

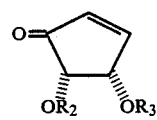  (IXb)

Compounds made from enantiomers (IXa) or (IXb) will be designated by a letter (a or b) following the Roman numeral. Letter (a) will be used for compounds made from enantiomer (IXa) and letter (b) for compounds made from enantiomer (IXb)

The present invention is also directed to a process for preparing enantiomerically pure compound (IX'b) which comprises:
protecting hydroxyl groups of D-mannose (XI)

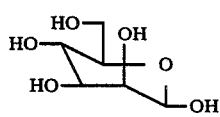  (XI)

to form compound (XII)

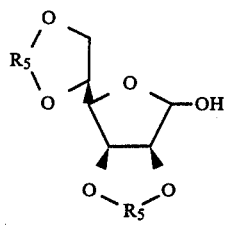
(XII)

wherein R₅ is an alkylidene or cycloalkylidene group, preferably a C₂ to C₆ alkylidene or cycloalkylidene group;

oxidizing the hydroxyl group of compound (XII) with an oxidizing agent such as Collin's reagent to form compound (XIII)

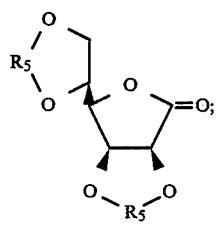
(XIII)

selectively deprotecting compound (XIII) under acidic conditions to form (XIV)

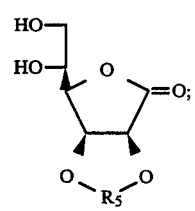
(XIV)

subjecting compound (XIV) to basic conditions, e.g., by adding sodium hydroxide, to form compound (VII′b)

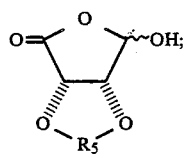
(VII′b)

reacting (VII′b) with an alcohol of the formula R₄OH wherein R₄ is as defined above to form (VIII′b)

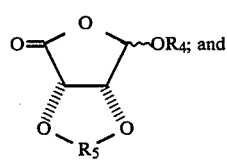
(VIII′b)

reacting (VIII′b) with a salt of dimethyl methylphosphonate to form enantiomerically pure (IX′b)

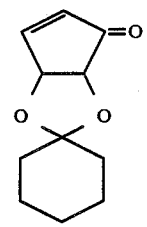
(IX′b)

The present invention is also directed to novel intermediates used in the preparation of the compound of the formula (I) which have the formula (IX″)

(IX″)

which includes the following two enantiomers

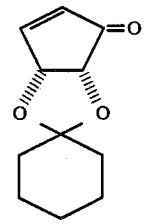
(IX″a)

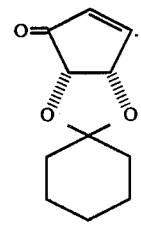
(IX″b)

EXAMPLE 1

(+)2,3-(Cyclohexylidenedioxy)-4-hydroxy-4-(2-propyloxy)butanoic acid lactone (VIIIa)

Method A

The 2,3-O-cyclohexylidene-L-erythruronolactone was synthesized according to the procedure of Beer et al, *Helvetica Chimica Acta,* 65, 2570 (1982) starting from the commercially available D-ribonolactone (V). The erythruronolactone (VIIa) was converted to compound (VIIIa) using a modification of the procedure of Chamberlin and Chung, *J. Org. Chem,* 50, 4425 (1985). The modified procedure uses 2-propanol instead of MeOH and the 3 angstrom molecular sieves are placed in a soxlet extractor rather than directly in the reaction medium. This modified procedure gave the desired compound (VIIIa) in 95% yield, whereas the Chamberlin and Chung procedure gave two major compounds (approximately 50% yield for each).

The L-erythruronolactone (VIIa) (19.2 gm, 90 mmol) was dissolved in 400 ml of dry 2-propanol and a soxlet extractor containing 50 gm of 3 angstrom sieves was connected, then the mixture was brought to a slow reflux. After 2 weeks (3-7 days gave 50-60% yield) the mixture was cooled and was concentrated to a solid. The solid was taken up in a minimum amount of hexane/Et$_2$O (5:1) and any solid (starting material) that remained was removed by filtration. The filtrate was applied to a silica gel column (60 gm) and eluted with hexane/Et$_2$O (5:1) giving 22.0 gm (95%) of the desired compound: bp 134°-7° C. at 1.25 mmHg; $[\alpha]_D$: +45.18° (c1.05,MeOH); Anal. Calc'd. for C$_{13}$H$_{20}$O$_5$: C,60.92; H,7.87. Found: C,60.58; H,7.90; IR (neat) 1799 cm$^{-1}$; $^1$H-NMR (CDCl$_3$) δ 5.54(s,1H,H-4), 4.81(d,1H,H-2,J=6 Hz), 4.51(d,1H,H-3,J=6 Hz), 4.02(heptet,1H,(CH$_3$)$_2$CH-O,J=7 Hz), 1.58(br. s, 10H,cylohex.), 1.24 and 1.18(2S,6H,2CH$_3$); Mass Spectrum (D-El,CH$_2$Cl$_2$) m/e 256(M+), 213(-Me$_2$CH), 81(cyclhexyl).

Method B

The following procedure for synthesizing compound (VIIIa) reduces the reaction time from 2 weeks to 2 hours.

The L-erythruronolactone (VIIa), (Beer et al, *Helv. Chim. Acta.*, 65, 2570 (1982)), (1.0 gm, 4.7 mmol) was dissolved in 50 ml of dry 2-propanol containing a catalytic amount of pyridinium p-toluenesulfonate (10 mole %, 0.12 gm, 0.47 mmol) and was refluxed for 1.5 hours. The mixture was then concentrated to a syrup which was then dissolved in 50 ml of Et$_2$O and extracted with H$_2$O (2X, 50 ml), brine, dried over Na$_2$SO$_4$ and filtered. The filtrate was concentrated and the syrup was dissolved in a minimum amount of hexane/Et$_2$O (5:1) which was applied to a small column of silica gel (5 gm) and eluted with hexane/Et$_2$O (5:1) to give 1.15 gm of compound (VIIIa) (97% yield). The physical data (optical rotation, bp, NMR, IR, Elemental Analysis) are identical to those reported in Method A.

(−)2,3-Cyclohexylidenedioxy-4-cyclopentenone (IX"a)

In an oven dried 500ml 3 neck flask (fitted with a septum and a 125 ml addition funnel) was added dimethyl methylphosphonate (3.98 gm, 31.4 mmol) in 200 ml of dry THF and the lactone (VIIIa) (8.07 gm, 31.4 mmol) dissolved in 25 ml of THF was poured into the addition funnel. The phosphonate solution was cooled to −78° C. with an acetone/dry ice bath, then n-butyl lithium (1.6M in hexane, 19.6 ml, 31.4 mmol) was added dropwise from a syringe over a 8-10 minute period. When the addition was complete the solution was stirred for 15 minutes and the lactone was added rapidly. The solution was stirred for 5 hours at −78° C. after which the dry ice bath was removed. When the solution came to room temperature (approximately 30 minutes), the mixture was poured into 500 ml of Et$_2$O containing 100 ml of H$_2$O and shaken, then the organic layer was separated. The aqueous layer was extracted with an additional 100 ml of Et$_2$O and the organic layers were combined. The Et$_2$O layer was washed with brine, dried over Na$_2$SO$_4$, filtered and concentrated (less than 50° C.) to an oil (crude, 6 gm, 90%). The oil was dissolved in Et$_2$O and added to a column of silica gel (10 gm) which was eluted with Et$_2$O giving 4.85 gm (80%) of colorless liquid. (Solidifies in the freezer and recrystallized from Et$_2$O /hexane): mp 65° C.; $[\alpha]_D$: 52.8° (c7.4, MeOH); Anal. Calc'd. for C$_{11}$H$_{14}$O$_3$: C, 68.04; H, 7.22. Found: C, 68.36; H, 7.44; IR (neat) 1734 cm$^{-1}$; $^1$H-NMR (CDCl$_3$) δ 7.60(dd,1H,H-4,J=7 Hz), 6.19(d,1H,H-5,J=7 Hz), 5.26(dd,1H,H-3,J=6 Hz), 4.41(d,1H,H-2,J=6 Hz), 1.58(multiplet,10H); Mass Spectrum (D-El,CH$_2$Cl$_2$) m/e 194(M+).

(−)2,3-Cyclohexylidenedioxy-4-cyclopenten-1-ol (Xa)

The cyclopentenone (IXa) (2.04 gm, 10.5 mmol) and CeCl$_3$.7H$_2$O (3.91 gm, 10.5 mmol) were added to 60 ml of methanol cooled to 0° C. then NaBH$_4$ (0.48 gm, 12.6 mmol) was added (foamed) and the mixture was allowed to stir for 20 minutes. The pH was then adjusted to 7.0 with 1N HCl, then 200 ml Et$_2$O was added and the organic layer was washed with a small amount of brine, the Et$_2$O layer was dried over Na$_2$SO$_4$, filtered and concentrated to a yellow liquid. The liquid was dissolved in a small amount CH$_2$Cl$_2$ and added to a silica gel column (5 gm) and the product was eluted to give 1.7 gm (83%) of a colorless liquid: $[\alpha]_D$: −23.59° (c4.45, MeOH); Anal. Calc'd. for C$_{11}$H$_{16}$O$_3$: C, 67.35; H, 8.16, Found: C, 66.96; H, 8.30; $^1$H-NMR(CDCl$_3$) δ 5.84(s,2H,H-4 and H-5), 4.96(d,1H,H-1,J=6 Hz), 4.69(t,1H,H-3,J=6 Hz), 4.53(dd,1H,H-2,J=6 Hz) 1.55(multiplet,10H,Cyclohexyl); Mass Spectrum (D-El,CH$_2$Cl$_2$) m/e 196(M+),81(cyclohexyl).

(−)2,3-Cyclohexylidenedioxy-1-p-toluenesulonyloxy cyclopent-4-ene (IIIa)

The cyclopentenol (Xa) (0.22 gm, 1.12 mmol) and p-toluenesulfonyl chloride (0.41 gm, 2.14 mmol) were dissolved in 10 ml CH$_2$Cl$_2$, then Et$_2$N (0.46 gm, 4.48 mmol) was added. The mixture was stirred or 24 hours at room temperature after which the mixture was extracted with H$_2$O, brine, dried over Na$_2$SO$_4$, filtered and concentrated to dryness. The solid was dissolved in a small amount of CH$_2$Cl$_2$/hexane (1:1) and loaded onto a 2 mm chromatotron (Model 7429T) plate (silica gel) which was eluted with CH$_2$Cl$_2$/hexane (1:1) to give 0.31 gm (80%) of pure product: mp 110°-111° C.; $[\alpha]_D$: −62.26° (c2.65,CHCl$_3$); Anal. Calc'd. for C$_{18}$H$_{22}$O$_5$S: C, 61.7; H, 6.33. Found: C, 61.49; H, 6.54; $^1$H-NMR(CDCl$_3$) δ 7.85(d,2H,aromatic,J=8 Hz), 7.27(d,2H,aromatic,J=8 Hz), 5.87(multiplet,2H,H-4 and H-5), 5.3(d,1H,H-1,J=5 Hz), 2.42(S,3H,CH$_3$), 1.50(multiplet,10H); Mass Spectrum (D-El,CH$_2$Cl$_2$) m/e 350(M+), 155(-toslytate), 81(cyclohexyl).

(−)6-Amino-9-(2',3'-cyclohexylidenedioxycyclopent-4'-envl)-purine (IVa, X=CH)

The tosylate (IIIa) (1.45 gm, 4.1 mmol) was dissolved in 3 ml of DMF and this solution was added to a solution of sodium adenine (II, X=CH) in 10 ml of DMF [Sodium adenine was prepared by adding NaH (80%, 0.35 gm, 12.3 mmol) to a slurry of adenine (1.66 gm, 12.3 mmol) in 10ml DMF]. The mixture was stirred for 1 to 2 days at 50° C., then the DMF was removed by distillation. The residue was taken up in CH$_2$Cl$_2$ (50ml) and the undissolved material was removed by filtration. The filtrate was concentrated to dryness and the solid was dissolved in a small amount of CH$_2$Cl$_2$/EtOH (9:1) and loaded onto a 4 mm chromatotron (Model 7429T) plate and 0.56 gm (45%) of compound (IVa, X=CH) was collected: mp 87° C.; $[\alpha]_D$: 200.95° (c2.1,MeOH); Anal. Calc'd for C$_{16}$H$_{19}$N$_5$O$_2$.¾H$_2$O: C, 59.06; H, 5.89; N, 21.53. Found: C, 59.11; H, 5.70; N, 21.40; $^1$H-NMR (CDCl$_3$) δ 8.36(s,1H,H-2), 7.68(s,1H,H-8), 6.58(br. s,2H,NH$_2$ (exchanged D$_2$O)), 6.33(dd,1H,H-4',J=6 Hz,J=2 Hz), 5.93(dd,1H,H-5',J=6 Hz,J=2 Hz), 5.63(d,1H,H-1'J=1 Hz), 5.49(d,1H,H-3,'J=6 Hz), 4.71(d,1H, H-2',J=6 Hz), 1.60(multiplet,10H); Mass (−)6-Amino-9-[trans-2'-trans-3'-dihydroxycyclopent-4'-enyl]-purine (Ia, X=CH)

Compound (IVa, X=CH) (313 mg, 1.0 mmol) was mixed with 20 ml of $H_2O$ and 1 ml of 6N HCl was added. The mixture was stirred at room temperature for 3–6 hours until tlc ($CH_2Cl_2$/EtOH, (9:1)) showed no starting material remained. The solution was concentrated to dryness (azeotroped with EtOH) and the solid was dissolved in 1–2 ml of $H_2O$ and applied to a Dowex 1×8-50(H+) column. The product was eluted using dilute ammonium hydroxide and concentrated to dryness. The compound was dried azeotropically with ethanol. Yield: 230 mg (98%); mp 175°–6° C.; $[\alpha]_D$: −170° (c1.0,$H_2O$); Anal. Calc'd. for $C_{10}H_{11}N_5O_2 \cdot H_2O$: C,47 8; H,5.17; N,27.87. Found: C,48.07; H,5.2; N,27.50; $^1$H-NMR (DMSO $d_6$+$D_2O$) δ 8.47(s,2H,H-2,H-8), 6.09(multiplet,2H,H-4' and H-5'), 5.45(d,1H,H-1',J=6 Hz), 4.55(d,1H,H-3',J=6 Hz), 4.25(dd,1H,H-2',J=6 Hz); Mass Spectrum (QP-E1-Probe) m/e 233($M^{+1}$), 216(-HO), 135(base,adenine).

EXAMPLE 2

(−)4-Amino-1-2',3'-cyclohexylidenedioxycyclopent-4'-envyl]-imidazo4,5c]pyridine (IVa, X=N)

Compound (IVa, X=N) was prepared in the same manner as (IVa, X=CH) starting from (IIIa) (170 mg, 0.5 mmol), except sodium adenine (II, X=CH) was replaced by sodium 4-aminoimidazo[4,5c]pyridine (II, X=N) (100 mg, 0.75 mmol), Krenitsky et al, *J. Med. Chem.*, 29, 138 (1986): Yield: 100 mg (67%); mp 156°–158° C.; $[\alpha]_D$: −164° (c0.5, MeOH); UV $_{max}$263 nm, 267 nm(sh), Anal. Calc'd. for $C_{17}H_{20}N_4O_2 \cdot \frac{1}{2}H_2O$: C,64.55; H,6.64; N,17.72. Found: C,64.60; H,7.00; N,17.48; $^1$H-NMR(CDCl$_3$+$D_2O$) δ 7.87(d,1H,H-6,J=6 Hz), 7.65(s,1H,H-2), 6.79(d,1H,H-7,J=6 Hz), 6.38(d,1H,H-4',J=5 Hz), 6.10(d,1H,H-5,'J=5 Hz), 5.36(multiplet, 1H,H-1' and H-3',J=6 Hz), 4.58(d,H-2',J=6 Hz), 1.62(multiplet,10H); Mass Spectrum (D-E1,$CH_2Cl_2$) m/e 312(M+), 134(3-deazaadenine),81(cyclohexyl).

(−)4-Amino-1-(trans-2'-trans-3'-dihydroxycyclopent-4'-envl)-imidazo[4.5c]pyridine (Ia, X=N)

Compound (IVa, X=N) (300 mg, 0.96 mol) was mixed with 20 ml of $H_2O$ and 1 ml of 6N HCl was added. The mixture was stirred at room temperature for 3–6 hours until tlc ($CH_2Cl_2$/EtOH, (9:1)) showed no starting material remained. The solution was concentrated to dryness (azeotroped with EtOH) and the solid was dissolved in 1–2 ml of $H_2O$ and applied to a Dowex 1×8-50(H+) column. The product was eluted using dilute ammonium hydroxide and concentrated to dryness. The compound was dried azeotropically with ethanol. Yield: 219 mg 98%); mp 140° C.; $[\alpha]_D$: −210° (d1.1,MeOH); UV $_{max}$263 nm, 267nm(sh). Anal. Calc'd. for $C_{11}H_{11}N_4O_2 \cdot$EtOH: C56.49; H,6.02; N,21.09. Found: C,56.89; H,6.20; N,21 39; $^1$H-NMR (DMSO $d_6$+$D_2O$) δ 8.03(s,1H,H-2), 7.64(d,1H,H-6,J=6 Hz), 6.76(d,1H,H-7,J=6 Hz), 6.13(multiplet,2H,H-4' and H-5'), 5.29(d,1H,H-1',J=5 Hz), 4.49(d,1H,H-3',J=5 Hz), 4.05(dd.,1H,H-2',J=5 Hz); Mass Spectrum (D-E1,MeOH) m/e 232(M+) peak match Δ=0.0007, 215(-HO), 134(base,3-deazaadenine).

EXAMPLE 3

2,3:5,6-O-Dicyclohexylidene-D-mannonolactone (XIII)

Commercially available D-mannose (XI) was converted into 2,3:5,6-O-Dicyclohexylidene-D-mannose (XII) by the procedure reported by Guthrie, *J. Chem. Soc.*, 853 (1959).

To a solution of pyridine (53 gm, 670 mmol) in 500 ml of $CH_2Cl_2$ was added in portions $CrO_3$ (33.5 gm, 335 mmol) which was then stirred at room temperature for 1.5 hours. The sugar (XII), was dissolved in 50 ml of $CH_2Cl_2$ and added rapidly to the pyridine-$CrO_3$ complex. After 1.5 hours the solution was decanted and the tar was thoroughly triturated with $Et_2O$ (2X, 200 ml). The combined organic layers were filtered through a pad of celite and the filtrate was concentrated. The residue was taken up in 250 ml of $Et_2O$ and extracted with dilute HCl (2×200 ml), $H_2O$ (3×200 ml), brine, dried over $Na_2SO_4$ and filtered. The filtrate was concentrated to dryness and the resulting solid was dissolved in a minimum amount of $Et_2O$ which was applied to a column of silica gel (30 gm) and eluted with $Et_2O$/hexane (1:1) to give the desired compound (XIII) (15.9 gm, 84% yield), mp 108°–109° C. (Guthrie et al, supra, mp 108°–110° C.).

2,3-O-Cyclohexylidene-D-mannonolactone (XIV)

The lactone (XIII) (4 gm, 12 mmol) was dissolved in 100 ml of EtOH and 100 ml of $H_2O$ and 2 grams of Dowex-50W (H+) was added. The mixture was stirred for 6 hours at 40° C. after which the resin was removed by filtration and the filtrate was concentrated. The oil which was obtained was dissolved in a minimum amount of EtOAc/hexane (1:1) and the solid (D-mannonolactone) that formed was removed by filtration. The filtrate was applied to a column of silica gel (10 gm) and the starting material (less than 200 mg) that remained was removed by eluting with 75 ml of EtOAc/hexane (1:1) and the desired compound was removed by eluting with EtOAc to give 2.6 gm of compound (XIV) as a viscous syrup (85% yield), $[\alpha]_D^{25}$+41.6° (0.6c, MeOH); IR (Nujol) 1780 cm$^{-1}$; $^1$H-NMR (CDCl$_3$, TMS) 4.97(d,1H,J=1 Hz), 4.55-3.6(multiplet,5H), 2.88 (br.s,2H,exchanged $D_2O$), 1.6(br.s.10H); MS(D-E1) M+258.

2,3-O-cyclohexylidene-D-erythruronolactone (VII'b)

A solution of compound (XIV) (2.6 gm, 10 mmol) and NaOH (0.48, 12 mmol) in 30 ml of $H_2O$ was heated at 40° C. until all the solid material dissolved. The mixture was then cooled to 0° C. and NaIO$_4$ (5.12 gm, 24 mmol) in 20 ml of $H_2O$ was added dropwise (the pH was maintained at approximately 7.0 with dilute NaOH) after the addition was complete the reaction was allowed to stir for 10 minutes. Then solid BaCl$_2$ (0.5 gm) was added and the resulting precipitate was filtered through a pad of celite. The filtrate was acidified to pH 3.0 with 2N HCl and the mixture was extracted with EtOAc (2×200 ml, 1×100 ml) and extract was washed with brine, dried over $Na_2SO_4$ and filtered. The filtrate was concentrated to give 1.97 gm of the desired compound (VII'b) (92% yield). $[\alpha]^{25}_D$+42° (1.1c, CHCl$_3$): The compound was identical (mp, NMR, IR) with the 2,3-O-cyclohexylidene-L-erythruronolactone which was previously reported by Beer et al, *Helv. Chim. Acta.*, 65, 2570 (1982), $[\alpha]_D$ −39.8° (1.65c, CHCl$_3$) for the opposite enantiomer).

(−)2,3-(Cyclohexylidenedioxy)-4-hydroxy-4-(2-propyloxy)butanoic acid lactone (VIII'b)

The D-erythruronolactone (VII'b) (1.0 gm, 4.7 mmol) was dissolved in 50 ml of dry 2-propanol containing a catalytic amount of pyridinium p-toluenesulfonate (10 mole %, 0.12 gm, 0.47 mmol) and was refluxed for 1.5 hours. The mixture was then concentrated to a syrup which was then dissolved in 50 ml of $Et_2O$ and extracted with $H_2O$ (2X, 50 ml), brine, dried over $Na_2SO_4$ and filtered. The filtrate was concentrated and the syrup was dissolved in a minimum amount of hexane/$Et_2O$ (5:1) which was applied to a small column of silica gel (5 gm) and eluted with hexane/$Et_2O$ (5:1) to give 1.16 gm of compound (VIII'b) (98% yield). $[\alpha]^{25}_D$−45.5° (5.75c, MeOH). The physical data (bp, NMR, IR) were identical to the opposite enantiomer (VIIIa) described above.

(+)2,3-Cyclohexylidenedioxy-4-cyclopentenone (IX"b)

In an oven dried 100 ml 3 neck flask (with a septum and 125 ml addition funnel connected) was added dimethyl methylphosphonate (0.24 gm, 2.0 mmol) in 20 ml of dry THF and the lactone (VIII'b) (0.5 gm, 2.0 mmol) dissolved in 10 ml of THF was poured into the addition funnel. The phosphonate solution was cooled to −78° C. with an acetone/dry ice bath, then n-butyl lithium (1.6M in hexane, 1.25 ml, 2.0 mmol) was added dropwise from a syringe over a 3-4 minute period. When the addition was complete, the solution was stirred for 15 minutes and the lactone was added rapidly. The solution was stirred for 2 hours at −78° C. after which the dry ice bath was removed. When the solution came to room temperature (approximately 30 minutes), the mixture was concentrated and the residue was dissolved in 50 ml of $Et_2O$ containing 10 ml of $H_2O$ and shaken, then the organic layer was separated. The aqueous layer was extracted with an additional 50 ml of $Et_2O$ and the organic layers were combined. The $Et_2O$ layer was washed with brine, dried over $Na_2SO_4$, filtered and concentrated (less than 50° C.) to an oil. The oil was dissolved in $Et_2O$ and added to a column of silica gel (5 gm) which was eluted with $Et_2O$ giving 0.30 gm (77%) of colorless liquid. (Solidifies in the freezer and recrystallized from $Et_2O$/hexane). $[\alpha]^{25}_D$ 50° (6.5c, MeOH).

The physical data were identical (mp, NMR, IR) to the opposite enantiomer compound (IX"a) described above.

EXAMPLE 4

The compound (Ib) can be synthesized in the same manner as compound (Ia) by substituting the compound (IX'b) obtained in Example 3 for the compound (IX"a) described in Example 1.

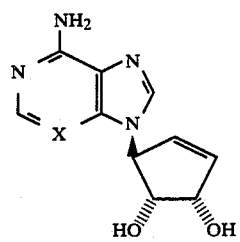
(Ib)

We claim:
1. A compound of the formula (I)

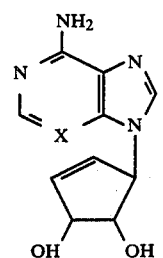
(I)

wherein X is =N— or =CH— or a physiologically acceptable salt or solvate thereof.
2. The compound of claim I which has the formula

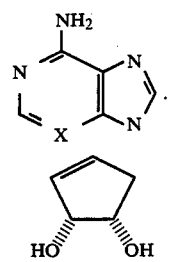
(Ia)

3. The compound of claim 2, wherein X is =N—.
4. The compound of claim 2, wherein X is =CH—.
5. An antiviral composition comprising an effective antiviral amount of the compound of claim 1, and a pharmaceutically effective carrier.
6. An antiviral composition comprising an effective antiviral amount of the compound of claim 2, and a pharmaceutically effective carrier.
7. The composition of claim 6, wherein X is =N—.
8. The composition of claim 6, wherein X is =CH—.
9. The composition of claim 7 which contains an effective anti poxvirus amount of said compound.
10. The composition of claim 8 which contains an effective anti poxvirus amount of said compound.
11. The composition of claim 7 which contains an effective anti reovirus amount of said compound.
12. The composition of claim 8 which contains an effective anti reovirus amount of said compound.
13. The composition of claim 7 which contains an effective anti measles, parainfluenza or vesicular stomatitis virus amount of said compound.
14. The composition of claim 8 which contains an effective anti measles, parainfluenza or vesicular stomatitis virus amount of said compound.
15. A method for treating viral infections which comprises administering an effective antiviral amount of the composition of claim 7 to a subject infected with poxvirus, reovirus, measles virus, parainfluenza virus or vesicular stomatitis virus.
16. A pharmaceutical composition comprising 0.1 to 99% by weight of the compound of claim 1 and a pharmaceutically effective carrier.

* * * * *